United States Patent [19]

Raynor

[11] Patent Number: 5,070,200

[45] Date of Patent: Dec. 3, 1991

[54] PROCESS FOR THE PREPARATION OF CHLOROAMINES

[75] Inventor: Robert J. Raynor, North Branford, Conn.

[73] Assignee: Olin Corporation, Cheshire, Conn.

[21] Appl. No.: 503,021

[22] Filed: Apr. 2, 1990

[51] Int. Cl.$^5$ ............... C07D 239/00; C07D 211/70; C07D 233/54; C07D 291/00
[52] U.S. Cl. .................... 544/242; 546/329; 548/341; 548/342; 549/74; 564/114; 564/116; 564/117; 564/118
[58] Field of Search ........... 544/242; 546/329; 548/341, 342; 549/74; 564/114, 116, 117, 118

[56] References Cited

U.S. PATENT DOCUMENTS 2,808,439  1/1957  Barrett et al. ............... 564/118
3,346,554 10/1967  Fuchs ........................ 534/587
4,677,227  6/1987  Osborg ....................... 564/118

Primary Examiner—Nicholas S. Rizzo
Assistant Examiner—Matthew V. Grumbling
Attorney, Agent, or Firm—F. A. Iskander; Donald M. Papuga

[57] ABSTRACT

Described herein is a process for chlorinating a primary amine by reacting the amine with an aqueous hypochlorous acid solution containing at least 5% by weight of hypochlorous acid, the process being conducted in an organic solvent.

19 Claims, No Drawings

PROCESS FOR THE PREPARATION OF CHLOROAMINES

This invention is directed to the preparation of chloroamines by reacting a pure and highly concentrated form of hypochlorous acid with at least one substituted methyl amine in an organic solvent. Also, this invention is directed to particular chloroamines.

Ullmann's Encyclopedia of Industrial Chemistry, Vol. A6, 5th Edition, 1986, in the section titled "Chloroamines", pages 553 to 558, defines chloroamines as inorganic or organic nitrogen compounds that contain one or more chlorine atoms attached to a nitrogen atom. The chloroamines are reactive intermediates capable of further reaction to produce a variety of products. Also, chloroamines have biocidal properties and are used as sanitizing, disinfecting, and bleaching agents.

N-chloro amines are generally prepared by halogenating the parent amine or reacting the parent amine with metal or alkyl hypochlorite, commonly in aqueous solution. The chlorination reaction is usually carried out under alkaline conditions to neutralize the hydrogen chloride which is generated.

For example, U.S. Pat. No. 3,346,554 describes the preparation of N-dichloro-amino compounds of the formula:

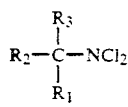

from amino compounds having the formula:

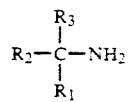

where $R_1$ is alkyl from 1 to 6 carbon atoms, $R_2$ is cycloalkyl of from 3 to 6 carbon atoms or alkyl of from 1 to 6 carbon atoms, and $R_3$ is a radical selected from the group consisting of —CN, —COOR, and —COOM, where R is an alkyl radical of from 1 to 6 carbon atoms and M is sodium or potassium; provided that $R_2$ and $R_3$ can be taken together and are a cycloalkyl of from 4 to 12 carbon atoms, and with the limitation that $R_1$ and $R_2$ will total to more than 4 carbon atoms.

Three methods are described in the patent for preparing the N-dichloro amino compounds. In the first method, an amino compound corresponding to the N-dichloro-amino compound sought to be prepared is reacted with chlorine in the presence of an acid acceptor and water while maintaining the pH of the reaction system at approximately neutral. The acid acceptor is stated to be an alkali metal or alkaline earth metal base.

In the second method, an amino compound can be chlorinated in the presence of water and a water immiscible organic solvent at a pH of about neutral.

In the third method, an amino compound can be reacted with chlorine in an organic solvent in the absence of water at about a neutral pH.

The N-dichloro amino compounds, described in U.S. Pat. No. 3,346,554, are formed into azo compounds by coupling in the presence of an organic solvent and a strong base.

However, under alkaline conditions, primary amines will react further to yield the corresponding mixture as illustrated by the following equation:

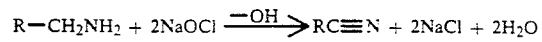

Therefore, there is a desire for a facile method to produce chloroamines, particularly from primary amines.

In this invention, it has been found that the use of a pure, acidic, aqueous solution of hypochlorous acid as the chlorinating agent produces both mono and dichloro substitution on the nitrogen atom of primary amines in a facile monomer. This reaction may be illustrated as follows:

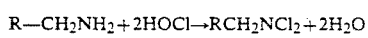

The amines which are chlorinated by the process of this invention are of the following formula:

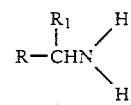

wherein R is selected from the group consisting of alkyl, aryl, and cycloalkyl containing 1 to 25 carbon atoms, heterocyclic, and substituted analogs thereof, and $R_1$ is hydrogen or alkyl of 1 to 6 carbon atoms.

Preferably, R is alkyl of 1 to 15 carbons, cyclohexyl, $C_1$-$C_6$ alkyl substituted cyclohexyl, phenyl, substituted phenyl, and heterocyclic. Illustrative radicals represented by R include the following:

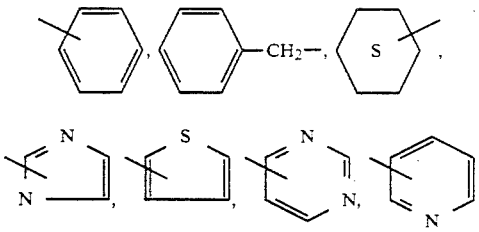

The chloroamines, according to this invention, are of the following formula:

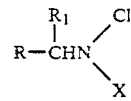

wherein X is H or Cl and R and $R_1$ are as defined above.

The hypochlorous acid used in the instant process may be characterized as a solution containing greater than 5% by weight of hypochlorous acid, preferably from about 25 to about 60%, and most preferably from about 30 to about 50% by weight of hypochlorous acid. The hypochlorous acid solution is substantially free of chloride, chlorate, and alkali metal ions.

The concentrated hypochlorous acid solution may be produced from a gaseous mixture comprised of chlorine monoxide, hypochlorous acid vapor, chlorine, and water vapor, which process comprises condensing the gaseous mixture at a temperature in the range of from about −5° C. to about +10° C.

In more detail, the process for producing the concentrated hypochlorous acid solution comprises reacting an aqueous alkali metal hydroxide, such as sodium hydroxide, potassium hydroxide, or lithium hydroxide in droplet form with chlorine gas. The reaction is conducted at temperatures sufficiently high enough to vaporize hypochlorous acid as it is produced and separate it from solid particles of alkali metal chloride which are also formed in the reaction. As gaseous mixtures having high concentrations of hypochlorous acid and chlorine monoxide are desired, highly concentrated aqueous solutions of the alkali metal hydroxide are used. Suitable concentrations include those in the range of from about 40 to about 80%, and preferably from about 45 to about 60% by weight of alkali metal hydroxide. A stoichiometric excess of chlorine above that required to form hypochlorous acid with all of the alkali metal hydroxide is used, for example from about 1 to about 20, and preferably from about 5 to about 10 times the stoichiometric proportion of chlorine is employed. Solid particles of alkali metal chloride are also produced during the reaction which have a wide range of particles sizes.

The gaseous mixture comprised of hypochlorous acid vapor, chlorine monoxide, chlorine, and water vapor used in the process contains high concentrations of HOCl and Cl$_2$O. The chlorine monoxide is formed by the conversion of HOCl vapors during the vaporization process according to the equation:

$$2HOCl \rightleftharpoons Cl_2O + H_2O \qquad (1)$$

The gaseous mixture also contains fine particles of the alkali metal chloride which are entrained. The solid particles may be removed by any suitable separation means, for example, by passing the gaseous mixture through a gas filter medium or through a solid separator such as a cyclone.

The gaseous mixture, now free of solids, is fed to a condenser. The condenser is operated at temperatures which produce concentrated aqueous solutions of hypochlorous acid without condensing undesirable amounts of chlorine or liquid chlorine monoxide. Suitable temperatures for operating the condensation process include those in the range of from about −5° C. to about +20° C.

The uncondensed gaseous mixture recovered from the condenser is substantially anhydrous as the water vapor originally present was condensed to form the aqueous hypochlorous acid solution. While the hypochlorous acid concentration is significantly reduced, the chlorine gas concentration is substantially the same as that in the original gaseous mixture fed to the condenser.

The concentrated hypochlorous acid solution is highly pure. The dissolved chlorine concentration in the hypochlorous acid solution of the present invention is less than about 2% by weight. The concentrated hypochlorous acid solution is essentially free of ionic impurities such as alkali metal, chloride, and chlorate ions. Concentrations of the chloride ion are less than about 50 parts per million; the alkali metal ion concentration is less than about 50 parts per million; and the chlorate ion concentration is no more than about 100 parts per million.

A process for producing hypochlorous acid is described in, for example, U.S. Pat. No. 4,146,578, incorporated in its entirety herein by reference.

The chlorination process of this invention may be carried out over a wide range of reaction conditions depending upon the primary amine to be chlorinated. Typical temperature ranges include those from about −20° C. to about 100° C., preferably from about 0° C. to about 25° C.

The chlorination of the primary amine is carried out in an organic solvent. The solvent is not critical, and any solvent capable of dissolving the starting primary amine, and which is inert to reaction with the hypochlorous acid, may be used. Typical solvents include methylene chloride, chloroform, ethyl acetate, and the like. The volume of solvent is typically equal to or greater than the volume of the hypochlorous acid solution. The reaction may be carried out for a period of about one minute up to a reaction time of about eight hours.

The molar ratio of the hypochlorous acid to starting primary amine is generally from 0.5 to 1 to about 10 to 1.

The chloroamines have biocidal properties and find use as sanitizing, disinfectant, and bleaching agents.

EXAMPLES

The following example illustrates the process of this invention and is presented without the intention of being limited thereby:

Preparation of Hypochlorous Acid Solution

The following represents a typical process of a concentrated hypochlorous acid solution useful in this invention:

A gaseous mixture containing an average concentration of 180.7 parts by weight of chlorine monoxide, 384.5 parts by weight of Cl$_2$, and 60.3 parts by weight of water vapor was continuously passed through a cyclone separator to remove any entrained solid particles of alkali metal chloride. The solid-free gaseous mixture at a temperature of 85°–90° C. was passed through a vertical shell and tube heat exchanger maintained at a temperature of about 0° C. and a pressure of about 3–4 torr gauge to condense a portion of the chlorine monoxide and substantially all of the water vapor to produce an aqueous hypochlorous acid solution containing 45 to 50% by weight of HOCl. The hypochlorous acid solution had a pH of about 1 and the dissolved chlorine concentration was determined to be about 1% by weight. An uncondensed gas mixture containing an average of 141.9 parts by weight of Cl$_2$O, 384.1 parts by weight of Cl$_2$ and 0.5 parts by weight of water was continuously removed from the condenser. The uncondensed gas mixture was passed through a heat exchanger to raise the temperature to about 100° C. and recycled to a generator used to produce the gaseous mixture of chlorine monoxide.

EXAMPLE 1

A stirred solution of 5.66 g. (0.05 m) of cyclohexyl methyl amine in 25 ml methylene chloride was cooled to 5° C. by means of an ice bath. To this solution was added, by means of a dropping funnel, 36.2 g. of a 29% aqueous solution of hypochlorous acid (0.20 m HOCl) over a 15 min. period. At the end of the addition, the temperature of the mixture had risen to 15° C. The ice bath was removed and the mixture stirred for an additional 15 minutes. The methylene chloride layer was separated, washed with a solution of sodium sulfite, and dried over sodium sulfate. The methylene chloride was removed on a rotary evaporator to give 7.3 of a light yellow oil. This oil was identified by nuclear magnetic resonance spectroscopy as N, N-dichloro cyclohexyl methyl amine.

COMPARATIVE EXAMPLE

A stirred solution of 5.66 g. (0.05 m) cyclohexyl methylamine in 25 ml methylene chloride was cooled to 5° C., and 0.5 g. of tetrabutylammonium hydrogen sulfate was added. To this cooled and stirred solution was added, by means of a dropping funnel, 149 ml of a 10% aqueous solution of sodium hypochlorite (0.22 m NaOCl) over a 15 minute period. The cooling bath was removed and the reaction mixture stirred for an additional 45 minutes. The methylene chloride layer was separated and dried over sodium sulfate. The methylene chloride was then removed on a rotary evaporator to give 4.1 g. of fluid residue identified by gas chromatography and nuclear magnetic resonance as cyclohexyl nitrile.

What is claimed is:

1. A process for chlorinating a primary amine which comprises reacting the amine with an aqueous hypochlorous acid solution containing at least 5% by weight of hypochlorous acid and being essentially free of chlorine, chlorate, and alkali metal ions, said process being conducted in an organic solvent.

2. A process as defined in claim 1, wherein the hypochlorous acid solution contains from about 5 to about 65% by weight of hypochlorous acid.

3. A process a defined in claim 1, wherein the hypochlorous acid solution contains from about 25 to about 60% by weight of hypochlorous acid.

4. A process a defined in claim 1, wherein the hypochlorous acid solution contains from about 30 to about 50% by weight of hypochlorous acid.

5. A process as defined in claim 1, wherein the primary amine is of the following formula:

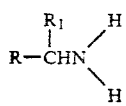

wherein R is selected from the group consisting of alkyl, aryl, and cycloalkyl containing from 1 to 25 carbon atoms, a heterocycle, and substituted analogs thereof, and $R_1$ is hydrogen or alkyl of 1 to 6 carbon atoms.

6. A process as defined in claim 5, wherein R is alkyl of 1 to 15 carbon atoms.

7. A process as defined in claim 6, wherein $R_1$ is hydrogen.

8. A process as defined in claim 5, wherein R is cyclohexyl.

9. A process as defined in claim 8 wherein $R_1$ is hydrogen.

10. A process as defined in claim 5, wherein R is phenyl.

11. A process as defined in claim 10, wherein $R_1$ is hydrogen.

12. A process as defined in claim 1 which is carried out at a temperature of from about $-20°$ C. to about $100°$ C.

13. A process as defined in claim 1 which is carried out at a temperature of from about $0°$ C. to about $25°$ C.

14. A process as defined in claim 1, wherein the molar ratio of hypochlorous acid to primary amine is from 0.5 to 1 to about 10 to 1.

15. A process for chlorinating a primary amine which comprises the following steps:
   (I) forming a hypochlorous acid solution from a gaseous mixture comprised of chlorine monoxide, hypochlorous acid vapor, chlorine, and water vapor comprising condensing the gaseous mixture at a temperature in the range of from about $-5°$ C. to about $+10°$ C., and
   (II) reacting said hypochlorous acid solution with a primary amine.

16. A process as defined in claim 15 wherein the hypochlorous acid solution contains from about 25 to about 60% by weight of hypochlorous acid.

17. A process as defined in claim 15 wherein the hypochlorous acid solution contains from about 30 to about 50% by weight of hypochlorous acid.

18. A process as defined in claim 15, wherein step (II) is carried out at a temperature of from about $-20°$ C. to about $100°$ C.

19. A chloroamine of the following formula:

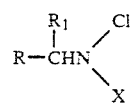

wherein R is cyclohexyl, $R_1$ is alkyl of 1 to 6 carbon atoms, and X is hydrogen or chlorine.

* * * * *